United States Patent [19]

Cramp et al.

[11] Patent Number: 5,480,857
[45] Date of Patent: Jan. 2, 1996

[54] HERBICIDAL 4-HETEROAROYLISOXAZOLE DERIVATIVES

[75] Inventors: Susan M. Cramp; Philip H. G. Smith, both of Essex, England

[73] Assignee: Rhone-Poulenc Agriculture Limited, Essex, England

[21] Appl. No.: 128,605

[22] Filed: Sep. 17, 1993

[30] Foreign Application Priority Data

Sep. 18, 1992 [GB] United Kingdom .................. 9219779

[51] Int. Cl.⁶ .......................... A01N 43/54; A01N 43/76; A01N 43/50; A01N 43/78
[52] U.S. Cl. ................... 504/239; 504/252; 504/260; 504/266; 504/270; 504/271; 544/333; 546/275; 548/204; 548/236; 548/248
[58] Field of Search .................................. 504/252, 260, 504/271, 239, 266, 270; 546/275; 544/333; 548/248, 204, 236

[56] References Cited

U.S. PATENT DOCUMENTS

| 4,636,513 | 1/1987 | Kammerer et al. | 514/326 |
|---|---|---|---|
| 4,995,902 | 2/1991 | Brunner | 504/260 |
| 5,125,956 | 6/1992 | Korte et al. | 504/252 |
| 5,260,262 | 11/1993 | Lee et al. | 504/252 |

FOREIGN PATENT DOCUMENTS

| 0410552 | 1/1991 | European Pat. Off. . |
|---|---|---|
| 0418175 | 3/1991 | European Pat. Off. . |
| 0461079 | 11/1991 | European Pat. Off. . |
| 0487357 | 5/1992 | European Pat. Off. . |

OTHER PUBLICATIONS

"The Pesticide Manual," tenth edition, ed. Clive Tomlin, The British Crop Protection Council and The Royal Society of Chemistry, 1994, pp. 888–889.

Derwent Abstract No. 91-349219/48 (abstract of JP-A-3232884, published Oct. 16, 1991).
Derwent Abstract No. 92-173209/21 (abstract of JP-A-04112876, published Apr. 14, 1992).
FARMACO, vol. 46, No. 6, issued 1991, Fossa et al., "5-substituted 4-isoxazolecarboxamides with platelet anti-aggregating and other activities", pp. 789–802. (Abstract only, CA115(21):232120k).

*Primary Examiner*—Allen J. Robinson
*Assistant Examiner*—Mary C. Cebulak
*Attorney, Agent, or Firm*—Burns, Doane, Swecker & Mathis

[57] ABSTRACT

4-heteroaroylisoxazole derivatives of formula I:

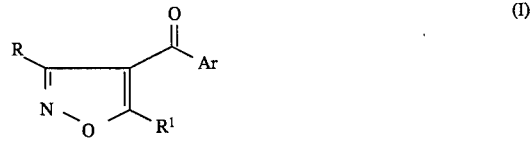

wherein:

Ar represents an optionally substituted group Het, wherein Het represents a first heterocyclic ring containing from one to four heteroatoms in the ring selected from oxygen, nitrogen and sulphur, which is optionally fused with a benzene, or carbocyclic or second heterocyclic ring (which is optionally saturated or partially saturated) to form a bicyclic system, wherein the first heterocyclic ring of the group Het is attached to the carbonyl group in the 4-position of the isoxazole ring;

R represents hydrogen or —$CO_2R^3$;

$R^1$ represents alkyl or haloalkyl or a cycloalkyl group optionally substituted by one or more groups $R^4$;

$R^3$ and $R^4$ independently represent alkyl or haloalkyl; agriculturally acceptable salts thereof and their use in weed control is described.

30 Claims, No Drawings

HERBICIDAL 4-HETEROAROYLISOXAZOLE DERIVATIVES

This invention relates to novel 4-heteroaroylisoxazole derivatives, compositions containing them and their use as herbicides.

Herbicidal 4-benzoylisoxazoles are described in European Patent Publication Nos. 0418175 and 0487357. Ethyl 5-methy-4-(pyridin-4-oyl)isoxazole-3-carboxylate is described as an intermediate in the synthesis of pharmacologically active compounds in J. Pharm. Sci., Vol. 80, p341–348 (1991).

The present invention provides 4-heteroaroylisoxazoles of formula I:

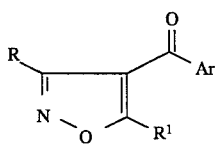

wherein:

Ar represents a group Het which is optionally substituted by one or more groups $R^2$, wherein Het represents a first heterocyclic ring containing from one to four heteroatoms in the ring selected from oxygen, nitrogen and sulphur, which is optionally fused with a benzene, or carbocyclic or second heterocyclic ring (which is optionally saturated or partially saturated) to form a bicyclic system, wherein the first heterocyclic ring of the group Het is attached to the carbonyl group in the 4-position of the isoxazole ring;

R represents the hydrogen atom or a group —$CO_2R^3$;

$R^1$ represents:
a straight- or branched- chain alkyl group containing from one to six carbon atoms which is optionally substituted by one or more halogen atoms; or
a cycloalkyl group containing from three to six carbon atoms optionally substituted by one or more groups $R^4$;

$R^2$ represents:
a halogen atom,
a straight- or branched- chain alkyl group containing from one to six carbon atoms which is substituted by a group —$OR^4$; or
a group selected from —OH, $R^4$, —$SR^5$, —$SOR^5$, —$SO_2R^5$, —O—$SO_2R^5$, —$CO_2R^4$, $COR^4$, —$OR^5$, —$NR^6R^7$, —$N(R^8)SO_2R^5$, nitro, cyano, —O$(CH_2)_m$—$OR^4$ and —(—$CR^9R^{10}$—$)_t$—$SO_2R^5$; or where $R^2$ is present on a heterocyclic or carbocyclic ring of the group Het, $R^2$ may also represent =O, =S, cyclic ketal or cyclic thioketal;

$R^3$ and $R^4$, which may be the same or different, each represent a straight- or branched- chain alkyl group containing from one to six carbon atoms which is optionally substituted by one or more halogen atoms;

$R^5$ represents:
a group $R^4$ or
phenyl optionally substituted by from one to five groups selected from halogen, $R^4$, —$CO_2R^4$, —$COR^4$, —$OR^4$, nitro, cyano and a group —O$(CH_2)_m$—$OR^4$;

$R^6$ and $R^7$, which may be the same or different, each represent the hydrogen atom or a straight- or branched-chain alkyl group containing from one to six carbon atoms which is optionally substituted by one or more halogen atoms;

$R^8$ represents:
the hydrogen atom;
a straight- or branched-chain alkyl, alkenyl or alkynyl group containing up to ten carbon atoms which is optionally substituted by one or more halogen atoms;

$R^9$ and $R^{10}$, which may be the same or different, each represents:
the hydrogen atom;
a straight- or branched-chain alkyl group containing up to 6 carbon atoms which is optionally substituted by one or more halogen atoms; or
phenyl optionally substituted by from one to five groups $R^{21}$ which may be the same or different;

m represents an integer from one to three;

t represents one, two or three;

$R^{21}$ represents:
a halogen atom;
a straight- or branched-chain alkyl group containing up to three carbon atoms which is optionally substituted by one or more halogen atoms; or
a group selected from nitro, cyano, —$OR^4$ and —$S(O)_pR^4$, where p is zero, 1 or 2;

with the proviso that when R represents —$CO_2Et$ and $R^1$ represents a methyl group, Ar is not unsubstituted pyridin-4-oyl, and agriculturally acceptable salts thereof, which possess valuable herbicidal properties.

In certain cases the substituents R, $R^1$, $R^2$, $R^3$, $R^4$, $R^5$, $R^6$, $R^7$, $R^8$, $R^9$, $R^{10}$, and $R^{21}$ contribute to optical isomerism and/or stereo isomerism. All such forms are embraced by the present invention.

By the term "agriculturally acceptable salts" is meant salts the cations of which are known and accepted in the art for the formation of salts for agricultural or horticultural use. Preferably the salts are water-soluble.

Suitable acid addition salts formed by compounds of formula I include salts with inorganic acids, e.g. hydrochlorides, sulphates, phosphates and nitrates and salts with organic acids, e.g. acetic acid.

In the group Het preferably the first heterocyclic ring contains from 4 to 7 ring atoms, and the carbocylic or second heterocyclic ring contains from 4 to 7 ring atoms.

Het may be aromatic or non-aromatic. Examples of the ring system Het include:

thienyl, furyl, pyrrolyl and their benzo-fused analogues;

oxazinyl, thiazinyl, pyrazinyl, pyrimidinyl, pyfidazinyl and their benzo-fused analogues;

thiazolyl, oxazolyl, imidazolyl and their benzo-fused analogues;

pyrazolyl, isoxazolyl, isothiazolyl and their benzo-fused analogues;

oxadiazolyl, thiadiazolyl, triazolyl and, where appropriate, their benzo-fused analogues;

pyridinyl, pyranyl, thiinyl and their benzo-fused analogues;

oxadiazinyl, thiadiazinyl, triazinyl and, where appropriate, their benzo-fused analogues;

tetrazolyl, piperidinyl, morpholinyl and piperazinyl.

In the compounds of formula I and their salts, Ar is thus most preferably a monocyclic or fused bicyclic, heterocyclic system Het having a heterocyclic first ring and an optional second ring, said second ring when present being fused to said first ring, said first ring being attached to the carbonyl group in the 4-position of the isoxazole ring, said first ring having from 1 to 4 hetero ring atoms and from 4 to 7 total ring atoms, said hetero ring atoms being selected from the group consisting of oxygen, nitrogen and sulphur, said first ring being aromatic or non-aromatic and being optionally substituted with from 1 to $4R^2$ groups, which are the same or different, said second ring having from 0 to 4 hetero ring atoms and from 4 to 7 total ring atoms, said hetero ring atoms when present being selected from the group consisting of oxygen, nitrogen and sulphur, said second ring being aromatic or non-aromatic and being optionally substituted with from 1 to $4R^2$ groups, which are the same or different; and the remaining structural variables are defined as above. Preferably, said heterocyclic first ring is attached via a ring carbon atom therein to the carbonyl group in the 4-position of the isoxazole ring.

A preferred class of compounds of formula I are those wherein $R^2$ represents:

a halogen atom, or a straight- or branched-chain alkyl group containing from one to six carbon atoms which is substituted by a group $-OR^4$;

a group selected from $R^4$, $-SR^5$, $-SOR^5$, $-SO_2R^5$, $-O-SO_2R^5$, $-CO_2R^4$, $-COR^4$, $-OR^5$, $-NR^6R^7$, $-NHSO_2R^5$, nitro, cyano and $-O(CH_2)_m-OR^4$.

A further preferred class of compounds of formula I are those wherein Ar is selected from the group consisting of pyridinyl optionally substituted by from one to four groups $R^2$ which may be the same or different; pyrimidinyl optionally substituted by from one to three groups $R^2$ which may be the same or different; thienyl optionally substituted by from one to three groups $R^2$ which may be the same or different; imidazolyl optionally substituted by one or two groups $R^2$ which may be the same or different; pyrazolyl optionally substituted by from one to three groups $R^2$ which may be the same or different; thiazolyl optionally substituted by one or two groups $R^2$ which may be the same or different; and oxazolyl optionally substituted by from one to four groups $R^2$ which may be the same or different; wherein $R^2$ is as hereinbefore defined.

A further preferred class of compounds of formula I are those wherein Ar is pyrazolyl optionally substituted by from one to three groups $R^2$ which may be the same or different; or more preferably Ar is selected from the group consisting of pyridinyl optionally substituted by from one to four groups $R^2$ which may be the same or different, and thienyl optionally substituted by one or two groups $R^2$ which may be the same or different, wherein $R^2$ is as hereinbefore defined.

Particularly preferred compounds of formula I are those wherein Ar represents pyridinyl optionally substituted by from one to four groups $R^2$ which may be the same or different.

Compounds of formula I wherein $R^1$ is a cycloalkyl group containing from three to six carbon atoms optionally substituted by one or more groups $R^4$ are also preferred, most preferably cyclopropyl.

A further preferred class of compounds of formula I because of their herbicidal properties are those having one or more of the following features:

$R^1$ represents:
  a straight- or branched- chain alkyl group containing from one to four carbon atoms;
  a cyclopropyl group optionally substituted by a group $R^4$;

$R^2$ represents a halogen atom or a group selected from $-SR^5$, $-SOR^5$, $-SO_2R^5$, $R^4$ and $-OR^5$;

the first heterocyclic ring of the group Het is substituted by one or two groups $R^2$ which may be the same or different.

Particularly important compounds include:
1. 5-cyclopropyl-4-(3,5-dichloropyridin-2-oyl)isoxazole;
2. 5-cyclopropyl-4-(5-methylsulphenylpyridin-2-oyl)isoxazole;
3. 5-cyclopropyl-4-(5-trifluoromethylpyridin-2-oyl)isoxazole;
4. 5-cyclopropyl-4-(5-methoxypyridin-2-oyl )isoxazole;
5. 5-cyclopropyl-4-(5-methylsulphonylpyridin-2-oyl)isoxazole;
6. 5-cyclopropyl-4-(2-methylsulphenylpyridin-3-oyl)isoxazole;
7. 5-cyclopropyl-4-(2-methylsulphinylpyridin-3-oyl)isoxazole;
8. 5-cyclopropyl-4-(2-methylsulphonylpyridin-3-oyl)isoxazole;
9. 5-cyclopropyl-4-(2-methoxypyridin-3-oyl)isoxazole;
10. 5-cyclopropyl-4-(3-methylthien-2-oyl)isoxazole;
11. 4-(3-bromopyridin4-oyl)-5-cyclopropylisoxazole;
12. 4-(3-chloro-5-trifluoromethylpyridin-2-oyl )-5-cyclopropylisoxazole;
13. 5-cyclopropyl-4-(2-ethoxypyridin-3-oyl)isoxazole;
14. 4-(3-chlorothien-2-oyl)-5-cyclopropylisoxazole;
15. 5-cyclopropyl-4-(5-ethoxy-1-methyl-3-trifluoromethylpyrazo-4-oyl)isoxazole;
16. 5-cyclopropyl-4-[5-(4-fluorophenylthio)-1-methyl-3-trifluoromethylpyrazol-4-oyl]isoxazole; and
17. 5-cyclopropyl-4-(1-ethyl-3-trifluoromethylpyrazol-4-oyl)isoxazole.

The numbers 1 to 17 are assigned to these compounds for reference and identification hereinafter.

Compounds of formula I may be prepared by the application or adaptation of known methods (i.e. methods heretofore used or described in the literature), for example as hereinafter described.

It is to be understood that in the descriptions of the following processes the sequences may be performed in different orders, and that suitable protecting groups may be required to achieve the compounds sought.

According to a feature of the present invention compounds of formula I in which R represents hydrogen may be prepared by the reaction of a compound of formula (II):

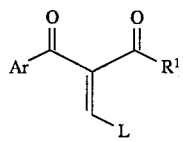

wherein L is a leaving group and Ar and $R^1$ are as hereinbefore defined, with a salt of hydroxylamine. Hydroxylamine hydrochloride is generally preferred. Generally L is O-alkyl, for example ethoxy, or N,N-dialkylamino, for example dimethylamino. The reaction is generally carried out in a solvent such as ethanol or acetonitrile, optionally in the presence of a base or acid acceptor such as triethylamine or sodium acetate.

According to a further feature of the present invention compounds of formula I in which R represents hydrogen may be prepared by the reaction of a compound of formula (III):

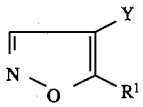 (III)

wherein $R^1$ is as hereinbefore described and Y represents a carboxy group or a reactive derivative thereof (such as a carboxylic acid chloride or carboxylic ester), or a cyano group, with an organometallic reagent of formula (IV):

Ar—M  (IV)

wherein Ar is as hereinbefore defined and M represents an alkali metal, a metal bonded to one or more ligands, or a Grignard group. Preferably M represents lithium, or a magnesium-containing Grignard group. The reaction is generally carried out in an inert solvent such as diethyl ether or tetrahydrofuran at a temperature from −78° C. to the reflux temperature of the mixture.

According to a further feature of the present invention compounds of formula I wherein R represents a group —$CO_2R^3$ may be prepared by the reaction of a compound of formula (V)

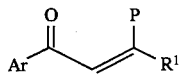 (V)

wherein Ar and $R^1$ are as hereinbefore defined and P is a leaving group, with a compound of formula $R^3O_2CC(X)$=NOH wherein $R^3$ is as hereinbefore defined and X is a halogen atom. Generally X is chlorine or bromine and P represents N,N-dialkylamino. The reaction is generally performed in an inert solvent such as toluene or dichloromethane either in the presence of a base such as triethylamine or a catalyst such as a 4 Angstrom molecular sieve or fluoride ion.

According to a further feature of the present invention compounds of formula I in which R represents a group —$CO_2R^3$ may be prepared by the reaction of a compound of formula (VI):

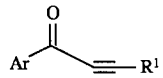 (VI)

wherein Ar and $R^1$ are as hereinbefore defined, with a compound of formula $R^3O_2CC(X)$=NOH wherein $R^3$ and X are as hereinbefore defined. The reaction is generally performed in an inert solvent such as toluene or dichloromethane optionally in the presence of a base such as triethylamine or a catalyst such as a 4 Angstrom molecular sieve or fluoride ion. The reaction can be carried out at a temperature between room temperature and the reflux temperature of the mixture.

According to a further feature of the present invention compounds of formula I wherein R represents —$CO_2R^3$ may be prepared by the reaction of the salt of a compound of formula (VII):

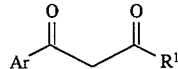 (VII)

wherein Ar and $R^1$ are as hereinbefore defined, with a compound of formula $R^3O_2CC(X)$=NOH wherein $R^3$ and X are as hereinbefore defined. Preferred salts include sodium or magnesium salts. The reaction may be performed in an inert solvent such as dichloromethane or acetonitrile at a temperature between room temperature and the reflux temperature of the mixture.

According to a further feature of the present invention compounds of formula I in which R represents hydrogen and Ar is not optionally substituted pyridyl, may be prepared by the reaction of a compound of formula (VIII):

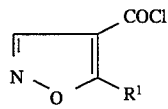 (VIII)

wherein $R^1$ is as hereinbefore defined, with a compound of formula Ar—H, wherein Ar is as hereinbefore defined excluding optionally substituted pyridyl. The reaction is generally performed in the presence of a Lewis acid catalyst such as aluminium trichloride, in an inert solvent at a temperature from 0° C. to the reflux temperature of the mixture.

Intermediates in the preparation of compounds of formula I may be prepared by the application or adaptation of known methods, for example as described hereinafter.

Compounds of formula (II) in which L represents O-alkyl or N,N-dialkylamino may be prepared by the reaction of the corresponding compound of formula (VII) with either a trialkyl orthoformate such as triethyl orthoformate or a dimethylformamide dialkylacetal such as N,N-dimethylformamide dimethyl acetal. The reaction with triethyl orthoformate is generally carried out in the presence of acetic anhydride at the reflux temperature of the mixture and the reaction with N,N-dimethylformamide dialkyl acetal is carried out optionally in the presence of an inert solvent at a temperature from room temperature to the reflux temperature of the mixture.

Compounds of formula (V) may be prepared by the reaction of a compound of formula (IX) with an acid chloride of formula (X):

 (IX)

 (X)

wherein Ar, $R^1$ and P are as hereinbefore defined. The reaction is generally carried out in the presence of an organic base such as triethylamine in an inert solvent such as toluene or dichloromethane at a temperature between −20° C. and room temperature.

Compounds of formula (VI) may be prepared by the metallation of the appropriate acetylene of formula (XI):

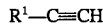 (XI)

wherein R¹ is as hereinbefore defined, followed by reaction of the metal salt thus obtained with an acid chloride of formula (X). The metallation is generally performed using n-butyl lithium in an inert solvent such as ether or tetrahydrofuran at a temperature from −78° C. to 0° C. The subsequent reaction with the acid chloride is carried out in the same solvent at a temperature between −78° C. and room temperature.

Compounds of formula (VII) may be prepared by the reaction of an ester of formula (XII):

ArCO₂Z    (XII)

wherein Ar is as hereinbefore defined and Z is an alkyl group, with a ketone of formula R¹C(O)CH₃, wherein R¹ is as hereinbefore defined in the presence of a base. Generally the base used is sodium hydride and the reaction is performed in an inert solvent at a temperature from 0° C. to reflux.

Compounds of formula (VII) may also be prepared by the reaction of a compound of formula (XIII):

ArCOCH₃    (XIII)

wherein Ar is as hereinbefore defined, with an ester of formula R¹CO₂Z, wherein R¹ and Z are as hereinbefore defined, in the presence of a base. Preferably Z represents a methyl, ethyl or t-butyl group. Generally the base used is sodium hydride and the reaction is performed in an inert solvent at a temperature from 0° C. to reflux.

Compounds of formula (VII) may also be prepared by the reaction of an acid chloride of formula (X) with the metal salt of a compound of formula (XIV):

wherein R¹ is as hereinbefore defined, to give a compound of formula (XV):

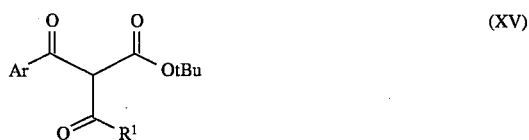

wherein Ar is as hereinbefore defined, which is decarboxylated to give a compound of formula (VII). Generally the reaction to produce the compound of formula (XIV) is performed in a solvent such as a lower alcohol, preferably methanol, in the presence of a metal, preferably magnesium. The decarboxylation is generally performed by refluxing the compound of formula (XV) in the presence of a catalyst, such as para-toluenesulphonic acid, in an inert solvent e.g. toluene.

Intermediates of formula (III), (IV), (VIII), (IX), (X), (XI), (XII), (XIII) and (XIV) are known or may be prepared by the application or adaptation of known methods.

The synthesis of compounds of formula (XII) and (XIII) in which Ar represents an optionally substituted pyridine group is described for example in 'The Chemistry of Heterocyclic Compounds', Volume 14, Part I, Chapter II. The synthesis of compounds of formula (XII) and (XIII) in which Ar represents an optionally substituted thiophene group is described for example in 'The Chemistry of Heterocyclic Compounds', Volume 44, Parts II and III, Chapter IV. The synthesis of compounds of formula (XII) and (XIII) in which Ar represents an optionally substituted thiazole group is described for example in 'The Chemistry of Heterocyclic Compounds'. Volume 34, Part I, Chapter IV. The synthesis of compounds of formula (XII) and (XIII) in which Ar represents an optionally substituted pyrimidine group is described for example in 'The Chemistry of Heterocyclic Compounds', Volume 16 and by Sakamoto and Yamanaka, Heterocycles, 1981, Volume 15, page 583. The synthesis of compounds of formula (XII) and (XIII) in which Ar represents an optionally substituted oxazole group is described for example in 'The Chemistry of Heterocyclic Compounds', Volume 45, Chapter I. The synthesis of compounds of formula (XII) and (XIII) in which Ar represents an optionally substituted imidazole group is described for example by Oliver and Sonnet, J. Organic Chem., 1973, Volume 38, page 1437 and by M. R. Grimmet, Advances in Heterocyclic Chem., Volume 27, page 241 and Volume 12, page 103 (same author). The synthesis of compounds of formula (XII) and (XIII) in which Ar represents an optionally substituted pyrazole group is described for example by Kost and Grandberg, Advances in Heterocylic Chemistry, 1966, Volume 6, page 347 and in 'The Chemistry of Heterocyclic Compounds'—"Pyrazoles, Pyrazolines, Pyrazolidines, Indazoles and Condensed Rings", edited by A. Weissberger.

Those skilled in the an will appreciate that some compounds of formula I may be prepared by the interconversion of other compounds of formula I and such interconversions constitute yet more features of the present invention. Examples of such interconversions are hereafter described.

According to a further feature of the present invention compounds in which R² represents —SOR⁵ or —SO₂R⁵ may be prepared by the oxidation of the sulphur atom of the corresponding compound in which R² represents —SR⁵ or —SOR⁵. The oxidation of the sulphur atom is generally carried out using for example 3-chloroperoxybenzoic acid in an inert solvent such as dichloromethane at a temperature from 40° C. to room temperature.

The following examples illustrate the preparation of compounds of formula I and the following reference examples illustrate the preparation of intermediates of the invention. In the present specification b.p. means boiling point; m.p. means melring point. Where the letters NMR appear the characteristics of the proton nuclear magnetic resonance spectrum follow. The specific examples are intended only as illustrative and are in no way limitative of the invention.

EXAMPLE 1

A mixture of hydroxylamine hydrochloride (0.4 g) and 3-cyclopropyl-1-(3,5-dichloropyridin-2-yl)-2-(dimethyl amino)methylenepropan-1,3-dione (1.68 g) in ethanol was stirred at room temperature overnight. The solvent was removed by evaporation and the residue was dissolved in dichloromethane. The resulting solution was washed with water, dried (anhydrous magnesium sulphate), filtered and evaporated. The residue was purified by column chromatography on silica eluted with a mixture of ethyl acetate and hexane to yield 5-cyclopropyl-4-(3,5-dichloropyridin-2-oyl)isoxazole (compound 1, 0.38 g) as a white solid, m.p. 81.9°–83.1° C.

By proceeding in a similar manner the following compounds of formula I were prepared from the appropriately substituted starting materials:

Compound 3: 5-cyclopropyl-4-(5-trifluoromethylpyridin-2-oyl)isoxazole, m.p. 74°–75° C.;

Compound 6: 5-cyclopropyl-4-(2-methylsulphenylpyridin-3-oyl)isoxazole, m.p. 95.4°–96.2° C.;

Compound 9: 5-cyclopropyl-4-(2-methoxypyridin-3-oyl)isoxazole, m.p. 112.5°–114° C.;

Compound 11: 4-(3-bromopyridin-4-oyl)-5-cyclopropylisoxazole, m.p. 92°–100° C.;

Compound 12: 4-(3-chloro-5-trifluoromethylpyridin-2-oyl)-5-cyclopropylisoxazole, m.p. 84°–86° C.;

Compound 13: 5-cyclopropyl-4-(2-ethoxypyridin-3-oyl)isoxazole, NMR (CDCl$_3$) δ1.2–1.4(m,7H), 2.8(s,1H), 4.4(q,2H), 7.0(m,1H), 7.8–7.9(dd,1H), 8.25(s,1H), 8.3(d, 1H);

Compound 14: 4-(3-chlorothien-2-oyl)-5-cyclopropylisoxazole, m.p. 72°–74° C.;

Compound 15: 5-cyclopropyl-4-(5-ethoxy-1-methyl-3-trifluoromethylpyrazol-4-oyl)isoxazole, m.p. 121°–123° C., starting from 1-(5-chloro-1-methyl-3-trifluoromethylpyrazol-4-yl)-3-cyclopropyl-2-ethoxymethylenepropan1,3-dione and introducing the 5-ethoxypyrazolyl group in-situ; Compound 16: 5-cyclopropyl-4-[5-(4-fluorophenylthio)-1-methyl-3-trifluoromethylpyrazol-4-oyl] isoxazole, m.p. 118°–120° C.;

Compound 17: 5-cyclopropyl-4-(1-ethyl-3-trifluoromethylpyrazol-4-oyl)isoxazole, m.p. 98°–100° C.

Compounds 14 to 17 were prepared using anhydrous sodium acetate as base.

By proceeding in a similar manner but using anhydrous sodium acetate (equimolar with the amount of hydroxylamine hydrochloride employed) as a base, the following compounds were prepared from the appropriately substituted starting materials:

Compound 2: 5-cyclopropyl-4-(5-methylsulphenylpyridin-2-oyl)isoxazole, m.p. 85°–86° C.;

Compound 4: 5-cyclopropyl-4-(5-methoxypyridin-2-oyl)isoxazole, 82°–84° C.;

Compound 10: 5-cyclopropyl-4-(3-methylthien-2-oyl)isoxazole, NMR (CDCl$_3$):δ1.1–1.32 (m,4H), 2.53 (s,3H), 2.65–2.8 (m,1H), 6.97 (d,1H) 7.45 (d,1H), 8.5 (s,1H).

EXAMPLE 2

3-Chloroperoxybenzoic acid, an oxidant (2.85 g), was added to a stirred solution of 5-cyclopropyl-4-(2-methylsulphenylpyridin-3-oyl)isoxazole (236 g) in dichloromethane at –20° C. A further quantity of the oxidant (0.14 g) was added after 5 minutes. The reaction mixture was stirred at –20° C. until analysis (by thin layer chromatography) indicated reaction was complete. The mixture was filtered and the filtrate was washed successively with aqueous sodium bicarbonate solution and aqueous sodium metabisulphite solution, dried (anhydrous magnesium sulphate), filtered and evaporated. The crude product was suspended in refluxing acetonitrile. The suspension was cooled to room temperature and filtered. The product was dried to yield 5-cyclopropyl-4-(2-methylsulphinylpyridin-3-oyl)isoxazole (compound 7, 2.0 g) as colourless crystals, m.p.148°–152.4° C.

By proceeding in a similar manner and increasing the number of equivalents of oxidant where necessary, the following compounds were prepared from the appropriately substituted starting materials:

Compounds 5: 5-cyclopropyl-4-(5-methylsulphonylpyridin-2-oyl)isoxazole, m.p. 142°–144° C.; and Compound 8: 5-cyclopropyl-4-(2-methylsulphonylpyridin-3-oyl)isoxazole, m.p. 111.2°–112° C.

Reference Example 1

A mixture of 3-cyclopropyl-1-(3,5-dichloropyridin-2-yl)propan-1,3-dione (1.3 g) and N,N-dimethylformamide dimethyl acetal (1.1 ml) in 1,4-dioxane was stirred at room temperature for 4 days and the solvent was evaporated to yield 3-cyclopropyl-1-(3,5-dichloropyridin-2-yl)-2-dimethylaminomethylenepropan-1,3-dione (1.73 g).

By proceeding in a similar manner the following compounds of formula II above were prepared from the appropriately substituted starting materials:

| Ar | R$^1$ | L | m.p. (°C.) |
|---|---|---|---|
| 2-Methylsulphenylpyridin-3-yl | Cp | —NMe$_2$ | 104.9–106.5 |
| 5-Trifluoromethylpyridin-2-yl | Cp | —NMe$_2$ | gum |
| 5-Methoxypyridin-2-yl | Cp | —NMe$_2$ | gum |
| 5-Methylsulphenylpyridin-2-yl | Cp | —NMe$_2$ | oil |
| 2-Methoxypyridin-3-yl | Cp | —NMe$_2$ | 95–98 |
| 3-Bromopyridin-4-yl | Cp | —NMe$_2$ | 147–149 (1) |
| 3-Chloro-5-trifluoromethylpyridin-2-yl | Cp | —NMe$_2$ | oil |
| 2-Chloropyridin-3-yl | Cp | —NMe$_2$ | oil |
| 1-Ethyl-3-trifluoromethylpyrazol-4-yl | Cp | —NMe$_2$ | oil |

Note:
Cp represents cyclopropyl
(1) Using toluene as solvent and heating at 80° C. for 4 hours.

Reference Example 2

A mixture of 1-cyclopropyl-3-(3-methylthien-2-yl)propan-1,3-dione (7.5 g) and triethylonhoformate (13.2 g) in acetic anhydride was stirred at reflux temperature for 7 hours and the solvent was evaporated. Residual solvent was removed azeotropically with toluene to yield 1-cyclopropyl-3-(3-methylthien-2-yl)propan-1,3-dione (11.32 g) as an orange oil which was not further purified.

By proceeding in a similar manner the following compounds were prepared from the appropriately substituted starting materials:
1-(3-chlorothien-2-yl)-3-cyclopropyl-2-ethoxymethylenepropan-1,3-dione;
1-(5-chloro-1-methyl-3-trifluoromethylpyrazo-4-yl)-3-cyclopropyl-2-ethoxymethylenepropan-1,3-dione; and
1-cyclopropyl-2-ethoxymethylene-3-[5-(4-fluorophenylthio)-1-methyl-3-trifluoromethylpyrazol-4-yl]-propan-1,3-dione.

Reference Example 3

Methyl cyclopropyl ketone (1.65 g) was added to a stirred suspension of sodium hydride (80% dispersion in oil; 0.6 g) in dry diethyl ether at 0° C. under an inert atmosphere. The mixture was stirred at 0° C. for one hour. Ethyl 3,5-dichloropyridine-2-carboxylate (2.16 g) was added and the mixture was stirred at 0° C. for 1 hour and then at room temperature overnight. Hydrochloric acid (2N) was added and the mixture was extracted with diethyl ether. The organic extracts were washed with water, dried (anthydrous magnesium sulphate), filtered and evaporated to give a brown gum which was purified by column chromatography on silica eluted with a mixture of ethyl acetate and hexane to yield 3-cyclopropyl-1-(3,5-dichloropyridin-2-yl)propan1, 3-dione (1.35 g) as a colourless solid, m.p. 50.2°–52.7° C.

By proceeding in a similar manner the following diones of formula (VII) above were prepared from the appropriately substituted starting materials;

| Ar | R¹ | m.p. (°C.) |
|---|---|---|
| 5-Methylsulphenylpyridin-2-yl | Cyclopropyl | 85–87 |
| 5-Trifluoromethylpyridin-2-yl | Cyclopropyl | 63–68 |
| 5-Methoxypyridin-2-yl | Cyclopropyl | 54–58 |
| 2-Methoxypyridin-3-yl | Cyclopropyl | 92–94 |
| 3-Methylthien-2-yl | Cyclopropyl | 55–58 |
| 3-Chlorothien-2-yl | Cyclopropyl | 50–55 |
| 2-Ethoxypyridin-3-yl | Cyclopropyl | oil (1) |
| 5-Chloro-1-methyl-3-trifluoromethylpyrazol-4-yl | Cyclopropyl | semi-solid (2) |

(1) NMR (CD$_3$SOCD$_3$) δ 1.3(d, 2H), 1.4(d, 2H), 1.7(t, 3H), 2.75(s, 1H), 4.75(q, 2H), 6.95(m, 1H), 7.2–7.3(q, 1H), 8.25(m, 1H), 8.4(m, 1H). The starting material for this reaction was ethyl 2-chloropyridine-3-carboxylate, and during the course of the reaction the chloro group was replaced by ethoxy.
(2) NMR (CDCl$_3$) δ 0.9(m, 2H), 1.05(m, 2H), 1.65(m, 1H), 3.8(s, 3H), 5.9(s, 1H), 15.7(broad s, 1H). This preparation was performed utilising dry tetrahydrofuran as solvent, and the product used directly in the next step.

Reference Example 4

A mixture of t-butyl 2-cyclopropanecarbonyl-3-(2-methylsulphenylpyridin-3-yl)-3-oxopropanoate (9.44 g) and 4-toluenesulphonic acid (0.4 g) in dry toluene was stirred at reflux for 5 hours then allowed to stand at room temperature overnight. The mixture was stirred at reflux for a further 5 hours, cooled to room temperature and taken up into ethyl acetate and water. The phases were separated and the aqueous phase was further extracted with ethyl acetate. The combined organic extracts were dried (anhydrous magnesium sulphate), filtered and evaporated to give 1-cyclopropyl-3-(2-methylsulphenylpyridin-3-yl)propan-1,3-dione (7.64 g) as a brown oil which was used without further purification.

By proceeding in a similar manner the following compounds were prepared from the appropriate starting materials:

1-cyclopropyl-3-[5-(4-fluorophenylthio)-1-methyl-3-trifluoromethylpyrazo-4-yl)propan-1,3-dione, m.p. 87°–89° C.;
1-cyclopropyl-3-(1-ethyl-3-trifluoromethylpyrazol-4-yl-)propan-1,3-dione, NMR (CDCl$_3$) δ0.9(m,2H), 1.1(m, 2H), 1.45(t,3H), 1.65(m,1H), 4.15(q,2H), 6.0(s,1H), 7.9(s,1H), 16.0 (broad s,1H);
1-(3-chloro-5-trifluoromethylpyridin-2-yl)-3-cyclopropylpropan-13-dione, m.p. 48°–51° C.; and
1-(3-bromopyridin-4-yl)-3-cyclopropylpropan-1,3-dione, m.p. 54°–55° C.

Reference Example 5

A suspension of magnesium (0.79 g) and iodine (1 crystal) in methanol was heated at reflux for approximately 1 hour. t-Butyl 3-cyclopropyl-3-oxopropanoate (5.53 g) was added to the refluxing suspension which was maintained at reflux for a further 50 minutes. After cooling to room temperature, solvent was evaporated and residual traces of methanol were azeotropically removed with toluene. The evaporation residue was redissolved in toluene and 2-methylsulphenyl-3-pyridinylcarbonyl chloride (5.63 g) was added as a slurry in toluene. The resulting suspension was stirred at room temperature overnight. Hydrochloric acid (2N) was added and the mixture was stirred for 45 minutes. The organic phase was separated, washed with water and brine, dried (anhydrous sodium sulphate), filtered and evaporated to yield t-butyl 3-cyclopropyl-2-(2-methylsulphenyl-3-pyridinylcarbonyl)-3-oxopropanoate (9.5 g) as a yellow oil which was used without further purification.

Similarly prepared were the following compounds:
t-butyl 3-cyclopropyl-2-[5-(4-fluorophenylthio)-1-methyl-3-trifluoromethy-4-pyrazolylcarbonyl]-3-oxopropanoate,
t-butyl 3-cyclopropyl-2-(1-ethyl-3-trifluoromethyl-4-pyrazolylcarbonyl)-3-oxopropanoate,
t-butyl 3-cyclopropyl-2-(3-chloro-5-trifluoromethyl-2-pyridinylcarbonyl)-3-oxopropanoate, and
t-butyl 2-(3-bromo-4-pyridinylcarbonyl)-3-cyclopropyl-3-oxopropanoate.

Reference Example 6

Methanethiol gas (7.9 g) was bubbled into a stirred suspension of sodium hydride (60% dispersion in oil; 6.0 g) in dry dimethylformamide with an exotherm of approximately 20° C. observed. A solution of methyl 5-nitro-2-pyridinecarboxylate (23.8 g) in dry dimethylformamide was added and the resulting suspension was stirred at 100° C. for five hours then left to stand at room temperature overnight. The solvent was evaporated. Water was added cautiously to the residue and the resulting solution was neutralised by the addition of hydrochloric acid (2N) and extracted with ethyl acetate. The combined extracts were washed with water, dried (anhydrous sodium sulphate), filtered and evaporated. The residue was purified by column chromatography on silica eluted with a mixture of ethyl acetate and hexane to give two crude products. The first product was triturated in a mixture of cyclohexane and diethyl ether to yield methyl 5-methylsulphenyl-2-pyridinecarboxylate (5.78 g) as a cream solid, m.p. 71°–73° C. The second product was methyl 5-methoxy-2-pyridinecarboxylate (2.67 g), obtained as a cream solid, m.p. 73°–74° C.

Reference Example 7

A mixture of 5-nitropyridine-2-carboxylic acid (33.91 g) and concentrated sulphuric acid (5 ml) in anhydrous methanol was heated at reflux for 20 hours. The solvent was evaporated and the residue was taken up in dichloromethane and water. The organic layer was dried (anhydrous sodium sulphate), filtered and the solvent evaporated to yield methyl 5-nitropyfidine-2-carboxylate (23.82 g) as an orange solid, m.p. 156°–159° C.

By proceeding in a similar manner the following compounds were prepared from the appropriately substituted starting materials:

| Compound | |
|---|---|
| Methyl 5-trifluoromethylpyridine-2-carboxylate | m.p. 85–88° C. |
| Methyl 2-methoxypyridine-3-carboxylate | yellow oil |
| Ethyl 3-methylthiophene-2-carboxylate | yellow oil |
| Ethyl 5-chloro-1-methyl-3-trifluoromethyl-pyrazole-4-carboxylate | yellow oil |

Note
(1) NMR (CDCl$_3$) 1.3(t, 3H), 3.85(s, 3H), 4.25(q, 2H), from 5-chloro-1-methyl-3-trifluoromethylpyrazole-4-carboxylic acid (L. F. Lee, F. M. Schleppnik, R. W. Salineider and D. H. Campbell in J. Het. Chem, 27, 243 (1990)). Concentrated hydrochloric acid was replaced by sulphuric acid in this preparation.

Reference Example 8

Diethyl 2-(5-nitropyridin-2-yl)malonate (67.47 g) was stirred in water and aqueous sodium hydroxide solution (2N) was added followed by potassium permanganate (42 g) causing the reaction temperature to rise to 60° C. Further portions of aqueous sodium hydroxide solution and potassium permanganate were added maintaining the reaction temperature at 60°–70° C. After the final addition, the suspension was stirred at 60° C. for 1.5 hours. The hot suspension was then filtered through 'Hyflo Supercel'. The filter cake was washed with aqueous sodium hydroxide solution (2N). On cooling to room temperature, the filtrate was carefully acidified to pH 1–2 with concentrated hydrochloric acid. The resulting precipitate was collected by filtration and dried to yield 5-nitropyridine-2-carboxylic acid (26.17 g) as a fawn solid, m.p. 210°–211° C.

By proceeding in a similar manner the following compounds were prepared:
5-trifluoromethylpyridine-2-carboxylic acid (hydrochloride salt), m.p.>300° C.; and
3-chloro-5-trifluoromethylpyridine-2-carboxylic acid (hydrochloride salt), m.p.>139° C.

Reference Example 9

Diethyl malonate (74 g) was added to a stirred suspension of sodium hydride (60% dispersion in oil; 18 g) in dry tetrahydrofuran under an inert atmosphere. The resulting suspension was stirred at reflux for one hour. The mixture was cooled to 60° C. and a solution of 2-chloro-5-nitropyridine (50 g) in dry tetrahydrofuran was added. The resulting red solution was stirred at reflux for 3 hours then allowed to stand at room temperature overnight. The volume of solvent was reduced by evaporation, water was added to the residue and the mixture was acidified to pH 1 with concentrated hydrochloric acid. The mixture was extracted with ethyl acetate, washed with water, dried (anhydrous magnesium sulphate), filtered and evaporated. The crude product was triturated in a mixture of cyclohexane and diethyl ether to yield diethyl 2-(5-nitropyridin-2-yl)malonate (56.5 g) as a yellow solid, m.p. 91.5°–93.5° C.

By proceeding in a similar manner the following compounds were prepared:
diethyl 2-(5-trifluoromethylpyridin-2-yl)malonate, obtained as a yellow oil;
diethyl 2-(3-chloro-5-trifluoromethylpyridin-2-yl)malonate b.p. 120°–122° C. (0.6–0.8 mbar).

Reference Example 10

Ethyl 1-ethyl-3-trifluoromethylpyrazole-4-carboxylate (2.17 g) was dissolved in ethanol and potassium hydroxide (1.06 g) in water was added. The reaction was stirred at room temperature overnight. Ethanol was removed under reduced pressure and the resulting residue partitioned between water and ether. The aqueous layer was separated, acidified with hydrochloric acid (2M) and extracted with ether. The combined organic extracts were dried over anhydrous magnesium sulphate and evaporated in vacuo to give 1-ethyl-3-trifluoromethylpyrazole-4-carboxylic acid as a white solid (1.86 g). NMR (CDCl$_3$) δ1.45(t,3H), 4.20(q,2H), 7.95(s, 1H).

Reference Example 11

Ethyl 3-trifluoromethylpyrazole-4-carboxylate (5 g), potassium carbonate (3.48 g) and ethyl iodide (2.3 ml) in acetonitrile were heated at reflux overnight. After cooling, ethyl acetate and water were added and the organic phase separated. The aqueous layer was extracted with ethyl acetate and the combined organic extracts were dried (magnesium sulphate) and evaporated under reduced pressure to give a yellow oil which was purified by crystallisation in hexane to produce 4-ethoxycarbonyl-1-ethyl-3-trifluoromethylpyrazole as white crystals (3.65 g), $^1$H NMR (CDCl$_3$) δ1.25(3H,t), 1.45(3H,t), 4.10(2H,q), 4.20(2H,q) 7.90(1H,s) ppm.

Reference Example 12

A mixture of 5-chloro-1-methyl-3-trifluoromethylpyrazole-4-carboxylic acid (2.0 g), 4-fluorothiophenol (1.66 g) and anhydrous potassium carbonate (3.26 g) was heated under reflux in acetonitrile with stirring for 4 hours. After filtration the filtrate was evaporated, acidified with dilute hydrochloric acid and extracted with ethyl acetate. The combined extract was dried (anydrous magnesium sulphate), filtered and evaporated in vacuo. Recrystallisation from ether/hexane gave 5-(4-fluorophenylthio)-1-methyl-3-trifluoromethylpyrazole-4-carboxylic acid (0.98 g) m.p. 190°–193.7° C. as a white solid.

Reference Example 13

3-Bromopyridine-4-carboxylic acid (5.0 g) was dissolved in thionyl chloride (50 ml) and the solution heated under reflux for 4 hours, cooled and evaporated in vacuo. Reevaporation of added toluene gave 3-bromopyridine4-carbonyl chloride, m.p.151°–154° C. (dec.) (5.45 g) as a green solid.

Similarly prepared were the following compounds:
3-chloro-5-trifluoromethylpyridine-2-carbonyl chloride, as a yellow semi-solid,
5-(4-fluorophenylthio)-1-methyl-3-trifluoromethylpyrazole-4-carbonyl chloride, as a brown semi-solid, and
1-ethyl-3-trifluoromethylpyrazole-4-carbonyl chloride as an oil.

The last two mentioned compounds were obtained by replacing the thionyl chloride with a solution of oxalyl chloride (1.2 equivalents) in 1,2-dichloroethane containing a few drops of N,N-dimethylformamide.

According to a feature of the present invention, there is provided a method for controlling the growth of weeds (i.e. undesired vegetation) at a locus which comprises applying to the locus a herbicidally effective amount of at least one 4-heteroaroylisoxazole derivative of formula I or an agriculturally acceptable salt thereof. For this purpose, the 4-heteroaroylisoxazole derivatives are normally used in the form of herbicidal compositions (i.e. in association with compatible diluents or carriers and/or surface active agents suitable for use in herbicidal compositions), for example as hereinafter described.

The compounds of formula I show herbicidal activity against dicotyledonous (i.e. broad-leafed) and monocotyledonous (e.g. grass) weeds by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula I may be used to control the growth of:

broad-leafed weeds, for example, *Abutilon theophrasti, Amaranthus retroflexus, Bidens pilosa, Chenopodium album, Galium aparine*, Ipomoea spp. e.g. *Ipomoea purpurea, Sesbania exaltata, Sinapis arvensis,*

*Solanum nigrum* and *Xanthium strumarium*, and grass weeds, for example *Alopecurus myosuroides, Arena fatua, Digitaria sanguinalis, Echinochloa crus-galli, Eleusine indica* and Setaria spp, e.g. *Setaria faberii* or *Setaria viridis*, and sedges, for example, *Cyperus esculentus*.

The amounts of compounds of formula I applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of formula I may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2.0 kg, of active material per hectare are particularly suitable.

The compounds of formula I may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non- directional fashion (e.g. by directional or non-directional spraying) to the weeds or to the soil in which they are expected to appear, before or after planting of the trees or plantations at application rates between 0.25 kg and 5.0 kg, and preferably between 0.5 kg and 4.0 kg of active material per hectare.

The compounds of formula I may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose.

When used to control the growth of weeds by pre-emergence application, the compounds of formula I may be incorporated into the soil in which the weeds are expected to emerge. It will be appreciated that when the compounds of formula I are used to control the growth of weeds by post-emergence application, i.e. by application to the aerial or exposed portions of emerged weeds, the compounds of formula I will also normally come into contact with the soil and may also then exercise a pre-emergence control on later-germinating weeds in the soil.

Where especially prolonged weed control is required, the application of the compounds of formula I may be repeated if required.

According to a further feature of the present invention, there are provided compositions suitable for herbicidal use comprising one or more of the 4-heteroaroylisoxazole derivatives of formula I or an agriculturally acceptable salt thereof, in association with, and preferably homogeneously dispersed in, one or more compatible agriculturally- acceptable diluents or carriers and/or surface active agents [i.e. diluents or carriers and/or surface active agents of the type generally accepted in the an as being suitable for use in herbicidal compositions and which are compatible with compounds of formula I]. The term "homogeneously dispersed" is used to include compositions in which the compounds of formula I are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula I.

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoridnoleates, quaternary ammonium derivatives, products based on condensates of ethylene oxide with alkyl and polyaryl phenols, e.g. nonyl- or octyl-phenols, or carboxylic acid esters of arthydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of formula I with solid diluents or by impregnating the solid diluents or carriers with solutions of the compounds of formula I in volatile solvents, evaporating the solvents and, if necessary, grinding the products so as to obtain powders. Granular formulations may be prepared by absorbing the compounds of formula I (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula I may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Hetbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are:

aqueous suspension concentrates which comprise from 10 to 70% of one or more compounds of formula I, from 2 to 10% of surface-active agent, from 0.1 to 5% of thickener and from 15 to 87.9% of water;

wettable powders which comprise from 10 to 90% Of one or more compounds of formula I, from 2 to 10% of surface-active agent and from 8 to 88% of solid diluent or carrier;

water soluble or water dispersible powders which comprise from 10 to 90% of one or more compounds of formula I, from 2 to 40% of sodium carbonate and from 0 to 88% of solid diluent;

liquid water soluble concentrates which comprise from 5 to 50%, e.g. 10 to 30%, of one or more compounds of formula I, from 5 to 25% of surface-active agent and from 25 to 90%, e.g. 45 to 85%, of water miscible solvent, e.g. dimethylformamide, or a mixture of water-miscible solvent and water;

liquid emulsifiable suspension concentrates which comprise from 10 to 70% of one or more compounds of formula I, from 5 to 15% of surface-active agent, from 0.1 to 5% of thickener and from 10 to 84.9% of organic solvent;

granules which comprise from 1 to 90%, e.g. 2 to 10% of one or more compounds of formula I, from 0.5 to 7%, e.g. 0.5 to 2%, of surface-active agent and from 3 to 98.5%, e.g. 88 to 97.5%, of granular carrier; and emulsifiable concentrates which comprise 0.05 to 90%, and preferably from 1 to 60%, of one or more compounds of formula I, from 0.01 to 10%, and preferably from 1 to 10%, of surface-active agent and from 9.99 to 99.94%, and preferably from 39 to 98.99%, of organic solvent.

Hetbicidal compositions according to the present invention may also comprise the compounds of formula I in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro-4-ethylamino-6-isopropylamino-1,3,5-triazine], bromoxynil [3,5-dibromo-4-hydroxybenzonitrile], chlortoluron [N'-(3-chloro-4-methylphenyl)-N,N-dimethylurea], cyanazine [2-chloro-4-(1-cyano-1-methylethylamino)-6-ethytamino-1,3,5-triazine], 2,4-D [2,4-dichlorophenoxy-acetic acid], dicamba [3,6-dichloro-2-methoxybenzoic acid], difenzoquat [1,2-dimethyl-3,5-diphenylpyrazolium salts], flampropmethyl [methyl N-2-(N-benzoyl-3-chloro-4-fluoroanilino)-propionate], fluometuron [N'-(3-trifluoromethylphenyl)-N,N-dimethylurea], isoproturon [N'-(4-isopropylphenyl)-N,N-dimethylurea], insecticides, e.g. synthetic pyrethroids, e.g. permethrin and cypermethrin, and fungicides, e.g. carbamates, e.g. methyl N-(1-butyl-carbamoyl-benzimidazol-2-yl)carbamate, and triazoles e.g. 1-(4-chloro-phenoxy)-3,3-dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the 4-heteroaroylisoxazole derivatives of formula I or, as is preferred, a herbicidal composition as hereinbefore described, and preferably a herbicidal concentrate which must be diluted before use, comprising at least one of the 4-heteroaroylisoxazole derivatives of formula I within a container for the aforesaid derivative or derivatives of formula I, or a said herbicidal composition, and instructions physically associated with the aforesaid container setting out the manner in which the aforesaid derivative or derivatives of formula I or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally lacquered, and plastics materials, bottles or glass and plastics materials and, when the contents of the container is a solid, for example granular, herbicidal compositions, boxes, for example of cardboard, plastics materials and metal, or sacks. The containers will normally be of sufficient capacity to contain amounts of the 4-heteroaroylisoxazole derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

The following Examples illustrate herbicidal compositions according to the present invention:

EXAMPLE C1

A soluble concentrate is formed from:

| | |
|---|---|
| Active ingredient (compound 1) | 20% w/v |
| Potassium hydroxide solution 33% w/v | 10% v/v |
| Tetrahydrofurfuryl alcohol (THFA) | 10% v/v |
| Water | to 100 volumes. | by stirring THFA, active ingredient (compound 1) and 90% volume of water and slowly adding the potassium hydroxide solution until a steady pH 7–8 was obtained then making up to volume with water.

Similar soluble concentrates may be prepared as described above by replacing the 4-heteroaroylisoxazole (compound 1) with other compounds of formula I.

EXAMPLE C2

A wettable powder is formed from:

| | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene sulphonate | 2% w/w |
| Microfine silicon dioxide | 3% w/w and |
| China clay | 37% w/w | by blending the above ingredients together and grinding the mixture in an air jet mill.

Similar wettable powders may be prepared as described above by replacing the 4-heteroaroylisoxazole (compound 1) with other compounds of formula I.

EXAMPLE C3

A water soluble powder is formed from:

| | |
|---|---|
| Active ingredient (compound 1) | 50% w/w |
| Sodium dodecylbenzenesulphonate | 1% w/w |
| Microfine silicon dioxide | 2% w/w |
| Sodium bicarbonate | 47% w/w | by mixing the above ingredients and grinding the above mixture in a hammer mill.

Similar water soluble powders may be prepared as described above by replacing the 4-heteroaroylisoxazole (compound 1) with other compounds of formula I.

Representative compounds of formula I have been used in herbicidal applications according to the following procedures.

METHOD OF USE OF HERBICIDAL COMPOUNDS a) General

Appropriate quantities of the compounds used to treat the plants were dissolved in acetone to give solutions equivalent to application rates up to 4000 g test compound per hectare (g/ha). These solutions were applied from a standard laboratory herbicide sprayer delivering the equivalent of 290 litres of spray fluid per hectare.

b) Weed control: Pre-emergence

The seeds were sown in 70 mm square, 75 mm deep plastic pots in non-sterile soil. The quantities of seed per pot were as follows:

| | Approx number of seeds/pot |
|---|---|
| Weed species | |
| 1) Broad-leafed weeds | |
| *Abutilon theophrasti* | 10 |
| *Amaranthus retroflexus* | 20 |
| *Galium aparine* | 10 |
| *Ipomoea purpurea* | 10 |
| *Sinapis arvensis* | 15 |
| *Xanthium strumarium* | 2. |
| 2) Grass weeds | |
| *Alopecurus myosuroides* | 15 |
| *Avena fatua* | 10 |
| *Echinochloa crus-galli* | 15 |
| *Setaria viridis* | 20. |
| 3) Sedges | |
| *Cyperus esculentus* | 3. |
| Crop | |
| 1) Broad-leafed | |
| Cotton | 3 |
| Soya | 3. |
| 2) Grass | |
| Maize | 2 |
| Rice | 6 |
| Wheat | 6. |

The compounds of the invention were applied to the soil surface, containing, the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control:Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

| Weed species | Number of plants per pot | Growth stage |
|---|---|---|
| 1) Broad leafed weeds | | |
| *Abutilon theophrasti* | 3 | 1–2 leaves |
| *Amaranthus retroflexus* | 4 | 1–2 leaves |
| *Galium aparine* | 3 | 1st whorl |
| *Ipomoea purpurea* | 3 | 1–2 leaves |
| *Sinapis arvensis* | 4 | 2 leaves |
| *Xanthium strumarium* | 1 | 2–3 leaves. |
| 2) Grass weeds | | |
| *Alopecurus myosuroides* | 8–12 | 1–2 leaves |
| *Avena fatua* | 12–18 | 1–2 leaves |
| *Echinochloa crus-galli* | 4 | 2–3 leaves |
| *Setaria viridis* | 15–25 | 1–2 leaves. |
| 3) Sedges | | |
| *Cyperus esculentus* | 3 | 3 leaves. |

| Crops | Number of plants per pot | Growth stage |
|---|---|---|
| 1) Broad leafed | | |
| Cotton | 2 | 1 leaf |
| Soya | 2 | 2 leaves. |
| 2) Grass | | |
| Maize | 2 | 2–3 leaves |
| Rice | 4 | 2–3 leaves |
| Wheat | 5 | 2–3 leaves |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

When applied either pre- or post- emergence at 4 kg/ha or less, compounds 1 to 17 gave at least 80% control of one or more weed species.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound of the formula:

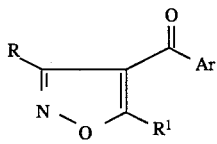

(I)

or an agriculturally acceptable salt thereof, wherein:

Ar is a monocyclic or fused bicyclic, heterocyclic system Het having a heterocyclic first ring and an optional second ring, said second ring when present being fused to said first ring, said first ring being attached to the carbonyl group in the 4-position of the isoxazole ring, said first ring having from 1 to 4 hetero ring atoms and from 4 to 7 total ring atoms, said hetero ring atoms being selected from the group consisting of oxygen, nitrogen and sulphur, said first ring being aromatic or non-aromatic and being optionally substituted by from 1 to 4 $R^2$ groups, which are the same or different, said second ring having from 0 to 4 hetero ring atoms and from 4 to 7 total ring atoms, said hetero ring atoms when present being selected from the group consisting of oxygen, nitrogen and sulphur, said second ring being aromatic or non-aromatic and being optionally substituted by from 1 to 4 $R^2$ groups, which are the same or different;

R is hydrogen;
cycloalkyl having from three to six carbon atoms, optionally substituted by one or more groups $R^4$;

$R^2$ is:
halogen;
straight- or branched-chain alkyl having up to six carbon atoms, substituted by a group $-OR^4$;
$-OH$, $R^4$, $-SR^5$, $-SOR^5$, $-SO_2R^5$, $-O-SO_2R^5$, $-CO_2R^4$, $-COR^4$, $-OR^5$, $-NR^6R^7$, $-N(R^8)SO_2R^5$, nitro, cyano, $-O(CH_2)_m-OR^4$ or $-(-CR^9R^{10}-)_t-SO_2R^5$;
provided that when said optional second ring of Het is non-aromatic, then $R^2$ can also be $=O$, $=S$, cyclic ketal or cyclic thioketal;

$R^3$ and $R^4$ which are the same or different, are each straight- or branched-chain alkyl having up to six carbon atoms, optionally substituted by one or more halogen;

$R^5$ is:
a group $R^4$; or
phenyl optionally substituted by from one to five members selected from the group consisting of halogen, $R^4$, $-CO_2R^4$, $-COR^4$, $-OR^4$, nitro, cyano and $-O(CH_2)_m-OR^4$;

$R^6$ and $R^7$ which are the same or different, are each hydrogen or straight- or branched-chain alkyl having up to six carbon atoms, optionally substituted by one or more halogen;

$R^8$ is:
hydrogen; or
straight- or branched-chain alkyl, alkenyl or alkynyl having up to ten carbon atoms, optionally substituted by one or more halogen;

$R^9$ and $R^{10}$, which are the same or different, are each:
hydrogen;
straight- or branched-chain alkyl having up to 6 carbon atoms, optionally substituted by one or more halogen; or
phenyl optionally substituted by from one to five groups $R^{21}$, which are the same or different;

m is one, two or three;

t is one, two or three; and $R^{21}$ is:
halogen;
straight- or branched-chain alkyl having up to three carbon atoms, optionally substituted by one or more halogen; or
a member selected from the group consisting of nitro, cyano, $-OR^4$ and $-S(O)_pR^4$ wherein p is zero, one or two.

2. The compound according to claim 1, wherein said heterocyclic first ring is thienyl, furyl, pyrrolyl, oxazinyl, thiazinyl, pyrazinyl, pyrimidinyl, pyridazinyl, thiazolyl, oxazolyl, imidazolyl, pyrazolyl, isoxazolyl, isothiazolyl, oxadiazolyl, thiadiazolyl, triazolyl, pyridinyl, pyranyl, thiinyl, oxadiazinyl, thiadiazinyl, triazinyl, tetrazolyl, piperidinyl, morpholinyl or piperazinyl, said first ring being optionally substituted by from 1 to 4 $R^4$ groups as defined in claim 1, said first ring being optionally fused to said second ring as defined in claim 1.

3. The compound according to claim 2, wherein said first ring is fused to said second ring, said second ring being a benzene ring which is optionally substituted by from one to four groups $R^2$, which are the same or different.

4. The compound according to claim 1, wherein Ar is pyridinyl, optionally substituted by from one to four groups $R^2$ which are the same or different; pyrimidinyl, optionally substituted by from one to three groups $R^2$ which are the same or different; thienyl, optionally substituted by from one to three groups $R^2$ which are the same or different; imidazolyl, optionally substituted by one or two groups $R^2$ which are the same or different; pyrazolyl, optionally substituted by from one to three groups $R^2$ which are the same or different; thiazolyl, optionally substituted by one or two groups $R^2$ which are the same or different; or oxazolyl, optionally substituted by from one to four groups $R^2$ which are the same or different.

5. The compound according to claim 1, wherein Ar is pyridinyl, optionally substituted by from one to four groups $R^2$ which are the same or different.

6. The compound according to claim 1, wherein Ar is pyrimidinyl, optionally substituted by from one to three groups $R^2$ which are the same or different.

7. The compound according to claim 1, wherein Ar is thienyl, optionally substituted by from one to three groups $R^2$ which are the same or different.

8. The compound according to claim 1, wherein Ar is imidazolyl, optionally substituted by one or two groups $R^2$ which are the same or different.

9. The compound according to claim 1, wherein Ar is pyrazolyl, optionally substituted by from one to three groups $R^2$ which are the same or different.

10. The compound according to claim 1, wherein Ar is thiazolyl, optionally substituted by one or two groups $R^2$ which are the same or different.

11. The compound according to claim 1, wherein Ar is oxazolyl, optionally substituted by from one to four groups $R^2$ which are the same or different.

12. The compound according to claim 1, wherein Ar is thienyl, optionally substituted by one or two groups $R^2$ which are the same or different.

13. The compound according to claim 1, wherein each $R^2$ is halogen, $R^4$, $-SR^5$, $-SOR^5$, $-SO_2R^5$, $-O-SO_2R^5$, $-CO_2R^4$, $-COR^4$, $-OR^5$, $-NR^6R^7$, $-NHSO_2R^5$, nitro, cyano, $-O(CH_2)_m-OR^4$ or straight- or branched-chain alkyl having up to six carbon atoms which is substituted by a group $-OR^4$.

14. The compound according to claim 2, wherein each $R^2$ is halogen, $R^4$, $-SR^5$, $-SOR^5$, $-SO_2R^5$, $-O-SO_2R^5$, $-CO_2R^4$, $-OR^5$, $-NR^6R^7$, $-NHSO_2R^5$, nitro, cyano, $-O(CH_2)_m-OR^4$ or straight- or branched-chain alkyl having up to six carbon atoms which is substituted by a group $-OR^4$.

15. The compound according to claim 3, wherein each $R^2$ is halogen, $R^4$, $-SR^5$, $-SOR^5$, $-SO_2R^5$, $-O-SO_2R^5$, $-CO_2R^4$, $-COR^4$, $-OR^5$, $-NR^6R^7$, $-NHSO_2R^5$, nitro, cyano, $-O(CH_2)_m-OR^4$ or straight- or branched-chain alkyl having up to six carbon atoms which is substituted by a group $-OR^4$.

16. The compound according to claim 4, wherein each $R^2$ is halogen, $R^4$, $-SR^5$, $-SOR^5$, $-SO_2R^5$, $-O-SO_2R^5$, $-CO_2R^4$, $-OR^5$, $-NR^6R^7$, $-NHSO_2R^5$, nitro, cyano, $-O(CH_2)_m-OR^4$ or straight- or branched-chain alkyl having up to six carbon atoms which is substituted by a group $-OR^4$.

17. The compound according to claim 1, wherein $R^1$ is cyclopropyl.

18. The compound according to claim 2, wherein $R^1$ is cyclopropyl.

19. The compound according to claim 4, wherein $R^1$ is cyclopropyl.

20. The compound according to claim 13, wherein $R^1$ is cyclopropyl.

21. The compound according to claim 16, wherein $R^1$ is cyclopropyl.

22. The compound according to claim 1, having at least one characteristic selected from the group consisting of:
(a) $R^1$ is cyclopropyl optionally substituted by a group $R^4$; $R^2$ is halogen, $-SR^5$, $-SOR^5$, $-SO_2R^5$, $R^4$ or $-OR^5$;
(c) said heterocyclic first ring is substituted by one or two groups $R^2$.

23. The compound according to claim 1 which is:
5-cyclopropyl-4-(3,5-dichloropyridin-2-oyl)isoxazole,
5-cyclopropyl-4-(5-methylsulphenylpyridin-2-oyl)isoxazole,
5-cyclopropyl-4-(5-trifluoromethylpyridin-2-oyl)isoxazole,
5-cyclopropyl-4-(5-methoxypyridin-2-oyl)isoxazole,
5-cyclopropyl-4-(5-methylsulphonylpyridin-2-oyl)isoxazole,
5-cyclopropyl-4-(2-methylsulphenylpyridin-3-oyl)isoxazole,
5-cyclopropyl-4-(2-methylsulphinylpyridin-3-oyl)isoxazole,
5-cyclopropyl-4-(2-methylsulphonylpyridin-3-oyl)isoxazole,
5-cyclopropyl-4-(2-methoxypyridin-3-oyl)isoxazole,
5-cyclopropyl-4-(3-methylthien-2-oyl)isoxazole,
4-(3-bromopyridin-4-oyl)-5-cyclopropylisoxazole,
4-(3-chloro-5-trifluoromethylpyridin-2-oyl)-5-cyclopropylisoxazole.
5-cyclopropyl-4-(2-ethoxypyridin-3-oyl)isoxazole,
4-(3-chlorothien-2-oyl)-5-cyclopropylisoxazole,
5-cyclopropyl-4-(5-ethoxy-1-methyl-3-trifluoromethylpyrazol-4-oyl)isoxazole,
5-cyclopropyl-4-[5-(4-fluorophenylthio)-1-methyl-3-trifluoromethylpyrazol-4-oyl]isoxazole, or
5-cyclopropyl-4-(1-ethyl-3-trifluoromethylpyrazol-4-oyl)isoxazole,
or an agriculturally acceptable salt thereof.

24. A herbicidal composition comprising a herbicidally effective mount of a compound of formula (I) as defined in claim 1 or an agriculturally acceptable salt thereof, and at least one member of the group consisting of an agriculturally acceptable diluent or carrier and an agriculturally acceptable surface active agent.

25. A herbicidal composition according to claim 24, comprising from about 0.05 to about 90% by weight of a compound of formula (I) or an agriculturally acceptable salt thereof.

26. A herbicidal composition according to claim 24, which is in liquid form and contains from about 0.05 to about 25 % by weight of surface-active agent.

27. A herbicidal composition according to claim 25, which is in liquid form and contains from about 0.05 to about 25 % by weight of surface-active agent.

28. A herbicidal composition according to claim 24, in the form of an aqueous suspension concentrate, a wettable powder, a water soluble or water dispersible powder, a liquid water soluble concentrate, a liquid emulsifiable suspension concentrate, a granule or an emulsifiable concentrate.

29. A method for controlling the growth of weeds at a locus which comprises applying to said locus a herbicidally effective amount of a compound of formula (I) as defined in claim 1 or an agriculturally acceptable salt thereof.

30. A method according to claim 29, wherein the locus is an area used, or to be used, for the growing of crops and the compound is applied at an application rate of from about 0.01 kg to about 4.0 kg per hectare.

* * * * *

UNITED STATES PATENT AND TRADEMARK OFFICE
CERTIFICATE OF CORRECTION

PATENT NO. : 5,480,857
DATED : January 2, 1996
INVENTOR(S) : Susan Mary CRAMP et al It is certified that error appears in the above-indentified patent and that said Letters Patent is hereby corrected as shown below:

In column 22, between lines 11 and 12, after "R is hydrogen;", insert the following:

-- $R^1$ is: --.

Signed and Sealed this

Seventeenth Day of June, 1997

Attest:

BRUCE LEHMAN

Attesting Officer

Commissioner of Patents and Trademarks